(12) United States Patent
Roifman et al.

(10) Patent No.: US 7,407,989 B2
(45) Date of Patent: Aug. 5, 2008

(54) COMPOUNDS USEFUL FOR MODULATING ABNORMAL CELL PROLIFERATION

(75) Inventors: Chaim Roifman, Toronto (CA); Peter Demin, Toronto (CA); Olga Rounova, Toronto (CA); Tom Grunberger, Toronto (CA)

(73) Assignee: The Hospital for Sick Children, Toronto, Ontario (CA)

( * ) Notice: Subject to any disclaimer, the term of this patent is extended or adjusted under 35 U.S.C. 154(b) by 0 days.

(21) Appl. No.: 11/723,261

(22) Filed: Mar. 19, 2007

(65) Prior Publication Data
US 2007/0185123 A1    Aug. 9, 2007

Related U.S. Application Data

(63) Continuation of application No. 10/940,010, filed on Sep. 14, 2004, now Pat. No. 7,202,383.

(51) Int. Cl.
*A61K 31/65* (2006.01)
(52) U.S. Cl. .................. 514/617; 514/252; 514/256; 514/307; 514/311; 514/357; 514/396; 514/412; 514/438; 514/461
(58) Field of Classification Search ............ 514/256, 514/311, 357, 307, 396, 412, 461, 617, 252.1, 514/438, 252; 544/242, 358; 546/139, 176, 546/329; 548/335.5, 503; 549/74, 491; 564/179
See application file for complete search history.

(56) References Cited

U.S. PATENT DOCUMENTS 4,673,684 A * 6/1987 Wakabayashi et al. ...... 514/327
7,202,383 B2 * 4/2007 Roifman et al. ............ 564/179

FOREIGN PATENT DOCUMENTS

| WO | WO 01/79158 | 10/2001 |
| WO | WO 02/26696 | 4/2002 |
| WO | WO 03/062190 | 7/2003 |

OTHER PUBLICATIONS

Roifman, C.M. et al., "Tyrenes: synthesis of new antiproliferative compounds with an extended conjugation," Bioorganic and Medicinal Chemistry, 12(2004), 3019-3026.
International Search Report for PCT/CA2005/001395, 2005.

* cited by examiner

*Primary Examiner*—Shailendra Kumar
(74) *Attorney, Agent, or Firm*—Omar A. Nassif

(57) ABSTRACT

There is described compounds of Formula I, and salts, solvates and hydrates thereof:

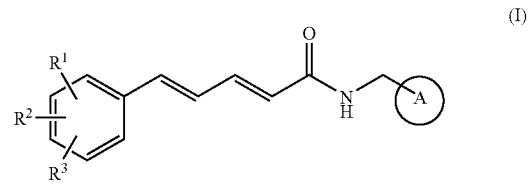

wherein: $R^1$, $R^2$ and $R^3$ are each independently selected from OH, $C_{1-6}$alkyl, $OC_{1-6}$alkyl, $OC(O)C_{1-6}$alkyl, $C(O)OC_{1-6}$alkyl, $NH_2$, $NH-C_{1-6}$alkyl, $N(C_{1-6}$alkyl$)(C_{1-6}$alkyl$)$, $C(O)NHC_{1-6}$alkyl, $C(O)N(C_{1-6}$alkyl$)(C_{1-6}$alkyl$)$, SH, $SC_{1-6}$alkyl, $NO_2$, $CF_3$, $OCF_3$ and halogen; and Ar is an aromatic or heteroaromatic group chosen from benzene, naphthalene, quinoline, isoquinoline, indole, pyridine, pyrasine, pyrimidine, imidazole, furan and thiophene, unsubstituted or substituted with 1-4 substituents independently selected from OH, $C_{1-6}$alkyl, $C_{1-6}$alkoxy, $C_{1-3}$alkylenedioxy, $NH_2$, $NH-C_{1-6}$alkyl, $N(C_{1-6}$alkyl$)(C_{1-6}$alkyl$)$, SH, $S-C_{1-6}$alkyl, $NO_2$, $CF_3$, $OCF_3$ and halogen. The compounds of Formula I are useful: in therapeutic methods and compositions for modulating cell proliferation, in diagnostic assays and as research tools.

5 Claims, No Drawings

US 7,407,989 B2

COMPOUNDS USEFUL FOR MODULATING ABNORMAL CELL PROLIFERATION

CROSS-REFERENCE TO RELATED APPLICATION

This application is a continuation of patent application Ser. No. 10/940,010, filed Sep. 14, 2004, now U.S. Pat. No 7,202,383.

BACKGROUND OF THE INVENTION

1. Field of the Invention

In one of its aspects, the present invention relates to a group of novel compounds, particularly useful for modulating abnormal cell proliferation. In another of its aspects, the present invention relates to a pharmaceutical composition comprising the novel compounds. In yet another of its aspects, the present invention relates to a method modulating cell proliferation using the novel compounds. In yet another of its aspects, the present invention relates to a process for production of the novel compounds.

2. Description of the Prior Art

A wide range of growth factors coordinate cell proliferation and differentiation. Malignant cells arise as a result of a stepwise progression of events that include the unregulated expression of growth factors or components of their signaling pathways. Tyrosine phosphorylation events initiated by receptor, cytoplasmic and nuclear kinases and regulated by phosphatases are central to these processes. Mutation, hyperactivation, translocation and overexpression of protein tyrosine kinases are all associated with tumorigenesis. In addition to increasing proliferative rates and immortalizing cells, overexpression of tyrosine kinases can lead to morphological transformation and cause anchorage independence, contributing to the promotion of migratory ability and possibly the induction of metastases.

Certain compounds with structures based upon mimicry of ATP or phosphotyrosine have been shown to be effective kinase inhibitors. Those based upon phosphotyrosine have been demonstrated to be the more specific tyrosine kinase inhibitors. Because of their ability to inhibit tyrosine phosphorylation, these compounds may alter cell responses to growth factors or other process driven by tyrosine kinase activity, including unregulated growth as the result of tyrosine kinase overexpression, mutation, or translocation. Inhibition of tyrosine kinases occupying a central role in proliferative signaling pathways, or in pathways regulating cell cytoskeletal structure, even temporary or incomplete inhibition, may be sufficient to switch a cancerous cell from a proliferative cycle into programmed cell death, or apoptosis. Death by apoptosis is most often observed upon effective treatment with tyrosine kinase inhibitors.

Selective inhibition of specific tyrosine kinases offers a method of targeting cancerous cell growth with a high degree of specificity and minimal toxicity to normally growing cells and tissues. Thus, specific inhibitors of tyrosine kinases have great potential as clinical anti-cancer treatments. A number of small molecules which act as tyrosine kinase inhibitors have been identified. For example, certain phenyl acrylonitrile compounds have been described as tyrosine kinase inhibitors, effective to inhibit cell proliferation. See, for example, any of U.S. Pat. Nos. 5,891,917, 5,217,999, 5,773,476, 5,935,993, 5,656,655, 5,677,329 and 5,789,427.

Inhibition of tyrosine kinases offers one mechanism by which cell proliferation can be inhibited. One of skill in the art will appreciate that other mechanisms of inhibition may also be involved.

Certain advances in the art are described in International Publication Number Number WO 01/79158 [Roifman et al. (Roifman #1)] International Publication Number Number WO 03/062190 [Roifman et al. (Roifman #2)].

While the teachings of Roifman #1 and Roifman #2 represent important advances in the art, there is an ongoing need in the art to identify further compounds that inhibit cell proliferation.

DISCLOSURE OF THE INVENTION

It is an object of the present invention to obviate or mitigate at least one of the above-mentioned disadvantages of the prior art.

In one of its aspects the present invention provides, the present invention provides a compound of Formula I, and salts, solvates and hydrates thereof:

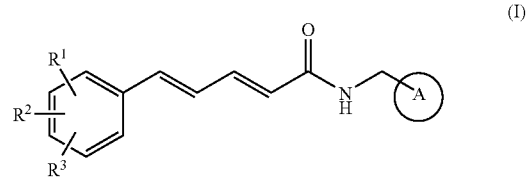

wherein:

$R^1$, $R^2$ and $R^3$ are each independently selected from OH, $C_{1-6}$alkyl, $OC_{1-6}$alkyl, $OC(O)C_{1-6}$alkyl, $C(O)OC_{1-6}$alkyl, $NH_2$, NH—$C_{1-6}$alkyl, $N(C_{1-6}$alkyl$)(C_{1-6}$alkyl$)$, $C(O)NHC_{1-6}$alkyl, $C(O)N(C_{1-6}$alkyl$)(C_{1-6}$alkyl$)$, SH, $SC_{1-6}$alkyl, $NO_2$, $CF_3$, $OCF_3$ and halogen;

Ar is an aromatic or heteroaromatic group chosen from benzene, naphthalene, quinoline, isoquinoline, indole, pyridine, pyrasine, pyrimidine, imidazole, furan and thiophene, unsubstituted or substituted with 1-4 substituents independently selected from OH, $C_{1-6}$alkyl, $C_{1-6}$alkoxy, $C_{1-3}$alkylenedioxy, $NH_2$, NH—$C_{1-6}$alkyl, $N(C_{1-6}$alkyl$)(C_{1-6}$alkyl$)$, SH, S—$C_{1-6}$alkyl, $NO_2$, $CF_3$, $OCF_3$ and halogen Non-limiting examples of preferred compounds of Formula I may be selected from the group comprising: 5-(4-Hydroxy-3-methoxyphenyl)-penta-2E,4E-dienoic acid benzylamide (CRD-81); 5-(3,4-Dihydroxyphenyl)-penta-2E,4E-dienoic acid benzylamide (CRD-82); 5-(4-Hydroxy-3,5-dimethoxyphenyl)-penta-2E,4E-dienoic acid 3,4-dihydroxybenzylamide (CRD-84); and 5-(4-Hydroxy-3-ethoxyphenyl)-penta-2E,4E-dienoic acid 3,4-dihydroxybenzylamide (CRD-85), the chemical structure of each of which is provided in the Examples below.

Another aspect of the present invention relates to a pharmaceutical composition comprising, as the active ingredient, one or more compounds of Formula I, together with a pharmaceutically acceptable carrier therefor.

In accordance with a further aspect of the present invention, there is provided a method for modulating cell proliferation, preferably inhibiting cell proliferation comprising administering an effective amount of a compound of the invention to a cell or animal in need thereof. The invention also includes a use of a compound of the invention to modulate cell proliferation, preferably inhibit cell proliferation.

The invention further includes a use of a compound of the invention to prepare a medicament to modulate cell proliferation, preferably inhibit cell proliferation.

In a preferred embodiment the present invention provides a method of inhibiting the proliferation of a cancer cell comprising administering an effective amount of a compound of the invention to a cell or animal in need thereof. The cancer cell treated may be any type of cancer including a leukemia, a lymphoma, myeloma, metastatic carcinoma, sarcoma or any other malignant transformation or any other malignancy. The invention also includes a use of a compound of the invention to modulate cancer cell proliferation, preferably inhibit cancer cell proliferation. The invention further includes a use of a compound of the invention to prepare a medicament to modulate cancer cell proliferation, preferably inhibit cancer cell proliferation.

In another aspect, the invention provides a method of modulating tyrosine kinase activity in a cell by administering an effective amount of a compound of the invention. In a further aspect, the invention provides a method of inhibiting tyrosine kinase activity in a cell by administering an effective amount of a compound of the invention. The present invention also provides a use of a compound of the invention to modulate, preferably inhibit, tyrosine kinase activity. The present invention further provides a use of a compound of the invention to prepare a medicament to modulate tyrosine kinase activity, preferably inhibit tyrosine kinase activity. It is appreciated that the inhibition of cell growth by the compounds of the invention may be effected by other mechanisms.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

The term "$C_{1-6}$alkyl" as used herein means, unless otherwise stated, straight and/or branched chain alkyl radicals containing from one to six carbon atoms and includes methyl, ethyl, propyl, isopropyl, t-butyl and the like.

The term "$C_{1-6}$alkoxy" as used herein means, unless otherwise stated, straight and/or branched chain alkoxy radicals containing from one to six carbon atoms and includes methoxy, ethoxy, propyloxy, isopropyloxy, t-butoxy and the like.

The term "$C_{1-4}$alkyl" as used herein means, unless otherwise stated, straight and/or branched chain alkyl radicals containing from one to four carbon atoms and includes methyl, ethyl, propyl, isopropyl, t-butyl and the like.

The term "$C_{1-4}$alkoxy" as used herein means, unless otherwise stated, straight and/or branched chain alkoxy radicals containing from one to four carbon atoms and includes methoxy, ethoxy, propyloxy, isopropyloxy, t-butoxy and the like.

The term "Ar" as used herein, means an unsubstituted or substituted aryl and/or heteroaryl group which, in the case of heteroaryl, may contain up to two heteroatoms, wherein the constituents are independently selected from the group consisting of OH, $C_{1-6}$alkyl, $C_{1-6}$alkoxy, $NH_2$, NH—$C_{1-6}$alkyl, $N(C_{1-6}$alkyl$)(C_{1-6}$alkyl$)$, SH, S—$C_{1-6}$alkyl, $NO_2$, $CF_3$, $OCF_3$ and halo, and includes unsubstituted or substituted phenyl, furyl, thienyl, indolyl, naphthyl, quinolyl and the like.

The term "halo" as used herein means halogen and includes chloro, flouro, bromo, iodo and the like.

The term "pharmaceutically acceptable salt" means an acid addition salt or a basic addition salt which is suitable for or compatible with the treatment of patients.

The term "compound of the invention" as used herein includes any compound of the Formula I as defined herein (including all salts, solvates or hydrates thereof) as well as a specific compound designated herein as CRD-81, CRD-82, CRD-84 and CRD-84 (including all salts, solvates or hydrates thereof).

The term "salt", as used in connection with the compounds of Formula I, is intended to encompass pharmaceutically acceptable acid addition salt and pharmaceutically acceptable base addition salt.

The term "pharmaceutically acceptable acid addition salt", as used herein, means any non-toxic organic or inorganic salt of any base compounds represented by Formula I or any their intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form.

In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt", as used herein, means any non-toxic organic or inorganic base addition salt of any acid compounds represented by Formula I or their intermediates. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art.

The term "solvate", as used herein, means a compound of Formula I, or a pharmaceutically acceptable salt of a compound of Formula I, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that inhibits cancer cell proliferation, an effective amount of an agent is, for example, an amount sufficient to achieve such a reduction in cancer cell proliferation as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate", as used herein, includes the inhibition or suppression of a function or activity (such as cell proliferation) as well as the enhancement of a function or activity.

To "inhibit" or "suppress" or "reduce" a function or activity, such as cancer cell proliferation, is to reduce the function or activity when compared to otherwise same conditions except for a condition or parameter of interest, or alternatively, as compared to another conditions.

The term "animal", as used herein, includes all members of the animal kingdom including humans and non-humans. The animal is preferably a human.

The term "a cell", as used herein, includes a plurality of cells. Administering a compound to a cell includes in vivo, ex vivo and in vitro treatment.

The term "cancer cells", as used herein, includes all forms of cancer or neoplastic disease.

The present invention includes within its scope, prodrugs of the compounds of the invention. In general, such prodrugs will be functional derivatives of a compound of the invention which are readily convertible in vivo into the compound from which it is notionally derived. Conventional procedures for the selection and preparation of suitable prodrugs are described, for example, in "Design of Prodrugs" ed. H. Bundgaard, Elsevier, 1985.

Some of the compounds of the invention may have at least one asymmetric center. Where the compounds according to the invention have one asymmetric center, the may exist as enantiomers. Where the compounds of the invention possess two or more asymmetric centers, they may additionally exist as diastereomers. It is to be understood that all such isomers and mixtures thereof in any proportion are encompassed within the scope of the present invention.

The present invention includes radiolabeled forms of compounds of the invention, for example, compounds of the invention labeled by incorporation within the structure $^3$H or $^{14}$C or a radioactive halogen such as $^{125}$I.

The compounds of the invention may, for example, be derived from an activated cinnamyl compound and an activated cyano-substituted methylene compound. A person skilled in the art, therefore, may wish to provide a generic name for the compounds of the invention based on the cinnamyl moiety. However, generic nomenclature based on the formed acrylonitrile moiety, for example, styryl acrylonitrile, would be more proper.

The compounds of the invention can be prepared by general process steps established in the art for production of unrelated compounds. Therefore, compounds of the invention may be prepared by the reaction sequence shown in Scheme 1:

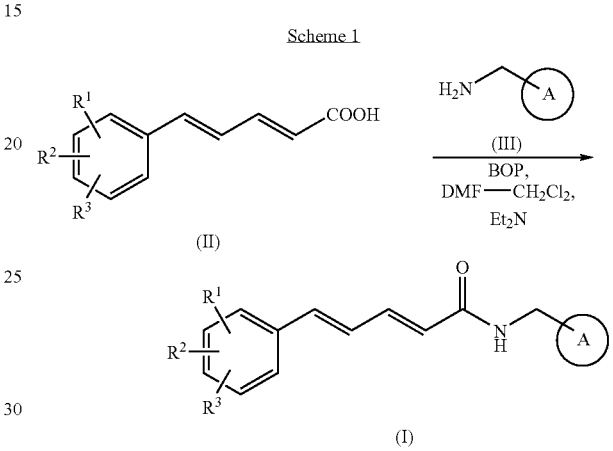

Compounds of the general Formula (I), useful in the practice of this invention can be prepared by the condensation of aryl-substituted 2E,4E-dienoic acids (II) with corresponding amine (III).

For example, these condensations may be carried out in appropriate solvents, such as DMF-dichloromethane, in the presence of various agents, useful in peptide chemistry, such as BOP (benzotriazol-1-yloxytris(dimethylamino)phosphonium hexafluorophosphate). Aryl-substituted 2E,4E-dienoic acids can be obtained by Wittig condensation of appropriate aryl-substituted cinnamaldehydes (IV) with methyl (triphenylphosphoranilydene)acetate.

At the end of this process, corresponding methyl Z,E-dienoate that is also formed in this conditions, can be converted into the desirable methyl E,E-dienoate (V) by treatment with iodine in dichloromethane. Methyl ester is hydrolyzed using standard procedures (Scheme 2).

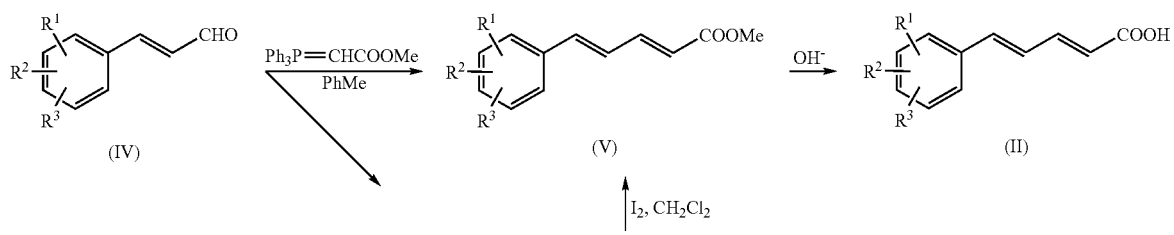

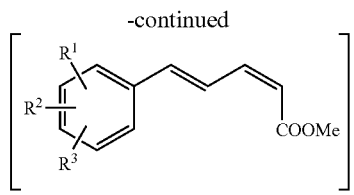

In some cases the condensation outlined above may have to be modified by use of protective groups, such as acetates or methyl ethers, to prevent side reactions. At the end of reaction sequence, the protective groups can be removed by processes analogous to those established in the art, for example as described in Greene T. W., Wuts P. G. M. Protective Groups in Organic Synthesis. John Wiley & Sons, Third Edition, 1999 (Scheme 3).

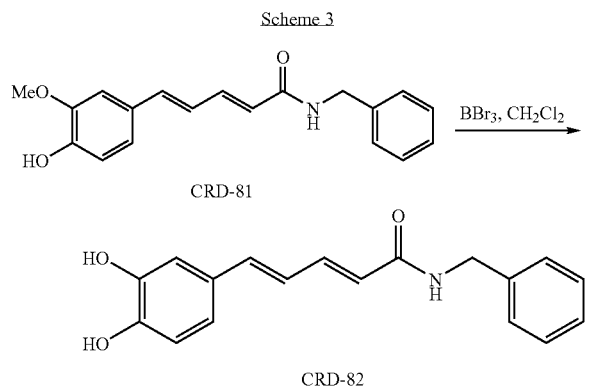

As stated above, an aspect of the present invention relates to a pharmaceutical composition comprising, as the active ingredient, one or more compounds of Formula I, together with a pharmaceutically acceptable carrier therefor.

The dosage administered of the active ingredient will vary depending on the use and known factors such as the pharmacodynamic characteristics of the particular substance, and its mode and route of administration; age, health, and weight of the individual recipient; nature and extent of symptoms, kind of concurrent treatment, frequency of treatment, and the effect desired.

By way of general guidance, a daily dosage of the active ingredient can be in the range of from about 0.01 to about 80 mg/kg of body weight, preferably from about 0.1 to about 20, more preferably from about 0.2 to about 10 mg/kg of body weight. Ordinarily a dose of from about 0.5 to about 50 mg/kg per day of the active ingredient divided doses one to multiple times a day, preferably up to four times per day, or in sustained release form is effective to obtain the desired results.

In the treatment methods and compositions of the present invention, the active ingredient described in detail herein is (are) typically administered for oral, topical, rectal, parenteral, local, inhalant or intracerebral use. In an embodiment of the invention, the substances are administered in intranasal form via topical use of suitable intranasal vehicles, or via transdermal routes, using forms of transdermal skin patches known to those of ordinary skill in that art. To be administered in the form of a transdermal delivery system, the dosage administration will be continuous rather than intermittent throughout the dosage regimen. The substances can also be administered by way of controlled or slow release capsule system and other drug delivery technologies.

A preferred form of administration is oral. For example, for oral administration in the form of a tablet or capsule, the active substance(s) can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral active substances can be combined with any oral, non-toxic, pharmaceutically acceptable inert carrier such as ethanol, glycerol, water, and the like. Suitable binders, lubricants, disintegrating agents, and colouring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum, and the like.

Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain colouring and flavouring agents to increase patient acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propyl-paraben, and chlorobutanol.

The active ingredient described in detail herein can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The active ingredient substances described in detail herein may also be coupled with soluble polymers which are targetable drug carriers. Examples of such polymers include polyvinylpyrrolidone, pyran copolymer, polyhydroxypropylmethacrylamide-phenol, polyhydroxyethylaspartamidephenol, or polyethyleneoxide-polylysine substituted with palmitoyl residues. The active ingredient substances may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. The substances can also be affixed to rigid polymers and other structures such as fullerenes or Buckeyballs.

Pharmaceutical compositions suitable for administration contain about 1 milligram to 1500 milligrams of active ingredient per unit. In these pharmaceutical compositions, the active ingredient will ordinarily be present in an amount of about 0.5-95% by weight based on the total weight of the composition.

Suitable pharmaceutical carriers and methods of preparing pharmaceutical dosage forms are described in Remington's Pharmaceutical Sciences, Mack Publishing Company, a standard reference text in art of drug formulation.

As hereinbefore mentioned, the inventors have prepared novel compounds of the Formula I. Accordingly, the present invention includes all uses of the compounds of the invention including their use in therapeutic methods and compositions for modulating cell proliferation, their use in diagnostic assays and their use as research tools.

In one aspect, the present invention provides a method for modulating cell proliferation comprising administering an effective amount of a compound of the invention to a cell or animal in need thereof. Preferably, the invention provides a method of inhibiting cell proliferation comprising administering an effective amount of a compound of the invention to a cell or animal in need thereof. In particular, the method of the invention is useful in inhibiting the proliferation of abnormal but not normal cells. Abnormal cells include any type of cell that is causative of or involved in a disease or condition and wherein it is desirable to modulate or inhibit the proliferation of the abnormal cell to treat the disease or condition. Examples of abnormal cells include malignant or cancerous cells as well as cell that over-proliferate in inflammatory conditions.

It has been determined that some of the compounds of the invention are very effective at killing cancer cells while at the same time they do not kill normal cells. These properties make the compounds of the invention extremely useful as anti-cancer agents. Accordingly, in one embodiment, the present invention provides a method of inhibiting the proliferation of a cancer cell comprising administering an effective amount of a compound of the invention to a cell or animal in need thereof.

The cancer cell that can be treated with a compound of the invention may be any type of cancer including, but not limited to, hematopoietic malignancies, including leukemias, lymphomas, and myelomas as well as other types of cancer including sarcomas, carcinomas, melanomas, adenomas, nervous system cancers and genitourinary cancers. Examples of leukemias include acute lymphoblastic leukemia (ALL), acute myclocytic leukemia (AML), chronic myeloid leukemia (CML), chronic lymphocytic leukemia (CLL) and juvenile myelo-monocytic leukemia (JMML). The types of ALL that may be treated with the compounds of the invention include cells that express a bcr-abl fusion protein, such as Philadelphia positive ALL cells, as well as Philadelphia negative ALL cells. Examples of lymphomas include B-cell Burkitt's lymphoma, Hodgkin's lymphomas, non-Hodgkin's lymphomas, including the Ki-1 positive anaplastic large cell lymphomas, T cell lymphomas and rare lymphomas such as the histiocytic lymphomas. Examples of myelomas include multiple myelomas.

Embodiments of the present invention will be described with reference to the following Examples that are provided for illustrative purposes only and should not be used to construe or limit the scope of the invention.

In the Examples, a number of standard methods and materials were used. $^1$H NMR spectra were obtained on a Varian Unity Plus spectrometer (USA) at 500 MHz with tetramethylsilane (TMS, Me$_4$Si) as an internal standard (O). Electrospray mass spectra were recorded on an API III Plus triple quadrupole mass spectrometer (USA), with a direct introduction of the samples into the ionization source. Thin layer chromatography was performed with UV-254 aluminum-backed TLC sheets of 0.25 mm thickness (Kieselgel 60 F$_{254}$, Merck, Germany). HPLC chromatograms and UV spectra were obtained on a model 600 liquid chromatograph (Waters, USA) with a model 996 PDA detector. The reagents were purchased from Aldrich (USA) and were used as received. Solvents were purchased from Caledon (Canada).

EXAMPLE 1

Methyl 5-(4-Acetoxy-3-methoxyphenyl)-penta-2E,4E-dienoate

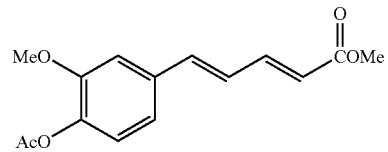

To a solution of 880 mg (4.0 mmol) of 4-acetoxy-3-methoxycinnamaldehyde in 100 mL of benzene, 2000 mg (6.0 mmol) of methyl (triphenylphosphoranilydene)acetate was added. The mixture was stirred at 80° C. for 4 h and passed through silica gel (eluent ethyl acetate-hexane, 1:1) to remove the excess of the Wittig reagent.

The solvents were evaporated, the residue was dissolved in 800 nL of dichloromethane, 12 (1 g) was added and the mixture was stirred at room temperature for 18 h. The mixture was worked up with 10% Na$_2$S$_2$O$_5$, the organic layer was dried with Na$_2$SO$_4$ and evaporated. The residue was crystallized from ethyl acetate-heptane.

The results were as follows:

a. Yield 990 mg (90%).

b. UV, $\lambda_{max}$ 245, 317 nm.

c. $^1$H-NMR (δ, ppm): 2.27 (s, 3H, OAc), 3.74 (s, 3H, COOMe), 3.90 (s, 3H, OMe), 6.08 (d, 1H, J=15.3 Hz, Hα olefinic), 7.09-7.15 (m, 3H, H$^5$+Hγ olefinic+Hδ olefinic), 7.18 (dd, 1H, J 1.9 and 8.2 Hz, H$^6$), 7.37 (d, 1H, J=1.9 Hz, H$^2$), 7.47 (dd, 1H, J 10.5 and 15.3 Hz, Hp olefinic).

d. MS (m/z, rel. intensity, %): 203.0 (62), 235.3 ([M+NH$_4$—OAc]+, 58), 245.3 ([M-OMe]+, 65), 277.0 ([M+H]$^+$, 100), 294.1 ([M+NH$_4$]+, 45), 299.2 ([M+Na]$^+$, 91), 335.2 ([M+OAc]+, 90).

EXAMPLE 2

Methyl 5-(4-Acetoxy-3,5-dimethoxyphenyl)-penta-2E,4E-dienoate

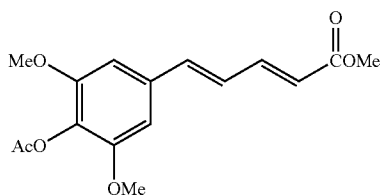

The compound was prepared based on the methodology used in Example I using 4-acetoxy-3,5-dimethoxycinnamaldehyde (500 mg, 2 mmol) and methyl (triphenylphosphoranilydene)acetate (1000 mg, 3 mmol).

The results were as follows:
a. Yield 525 mg (86%).
b. UV, $\lambda_{max}$ 245, 322 nm.
c. $^1$H-NMR (δ, ppm): 2.23 (s, 3H, OAc), 3.71 (s, 3H, COOMe), 3.83 (s, 6H, (OMe)$_2$), 6.04 (d, 1H, J=15.3 Hz, Hα olefinic), 6.96 (s, 2H, H$^{2+6}$), 7.02 (d, 1H, J=15.6 Hz, Hδ olefinic), 7.12 (dd, 1H, J 10.9 and 15.6 Hz, Hγ olefinic), 7.42 (dd, 1H, J 10.9 and 15.3 Hz, Hβ olefinic).
d. MS (m/z, rel.intensity, %): 233.2 ([M+NH$_4$—OAc—MeOH]$^+$, 44), 265.2 ([M+NH$_4$—OAc]+, 57), 275.2 ([M-OMe]+, 49), 307.2 ([M+H]$^+$, 100), 324.3 ([M+NH$_4$]$^+$, 75), 329.2 ([M+Na]$^+$, 25).

EXAMPLE 3

5-(4-Hydroxy-3-methoxyphenyl)-penta-2E,4E-dienoic acid

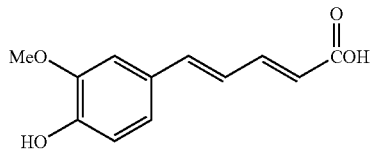

Methyl 5-(4-Acetoxy-3-methoxyphenyl)-penta-2E,4E-dienoate (400 mg, 1.45 mmol) [Example 1] was dissolved in 60 mL MeOH, 20 mL of 5% NaOH and 40 mL of water were added, and the mixture was stirred for 24 h at room temperature. The mixture was acidified to pH 2 with 5% HCl, methanol was evaporated and the compound was extracted with ethyl acetate. The organic layer was dried with Na$_2$SO$_4$ and evaporated.

The results were as follows:
a. Yield 320 mg (100%).
b. UV, $\lambda_{max}$ 252, 345 mm.

EXAMPLE 4

5-(4-Hydroxy-3,5-dimethoxyphenyl)-penta-2E,4E-dienoic acid

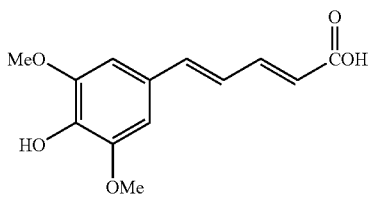

The compound was prepared using the methodology used in Example 4 using methyl 5-(4-Acetoxy-3,5-dimethoxyphenyl)-penta-2E,4E-dienoate (400 mg, 1.31 mmol) [Example 2].

The results were as follows:
a. Yield 328 mg (100%).
b. UV, $\lambda_{max}$ 255, 348 nm.

EXAMPLE 5

5-(4-Hydroxy-3-methoxyphenyl)-penta-2E,4E-dienoic acid benzylamide (CRD-81)

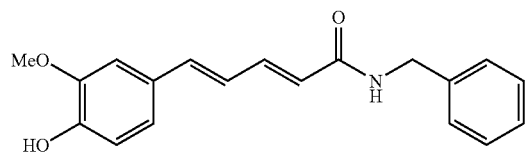

5-(4-Hydroxy-3-methoxyphenyl)-penta-2E,4E-dienoic acid (110 mg, 0.5 mmol) [Example 3] was dissolved in 100 mL of DMF. Triethylamine (101 µl, 1.0 mmol) was added, the mixture was cooled down to 0° C. and a solution of benzylamine (109 µl, 1.0 mmol) was added followed by addition of BOP reagent (331 mg, 0.75 mmol) in 50 mL of dichloromethane.

The mixture was stirred for 15 min at 0° C. and for 2 h at room temperature. Dichloromethane was evaporated, 5% HCl was added, and the product was extracted with ethyl acetate. The organic layer was dried with Na$_2$SO$_4$, evaporated, and the residue was purified on a column with silica gel, eluent ethyl acetate-hexane. The fractions contained the desired product were evaporated, the residue was dissolved in acetonitrile-water and lyophilized.

The results were as follows:
a. Yield 138 mg (89%).
b. UV, $\lambda_{max}$ 248, 340 mm.
c. MS (m/z, rel.intensity, %): 310.4 ([M+H]$^+$, 100), 332.5 ([M+Na]$^+$, 45).

EXAMPLE 6

5-(3,4Dihydroxyphenyl)-penta-2E,4E-dienoic acid benzylamide (CRD-82)

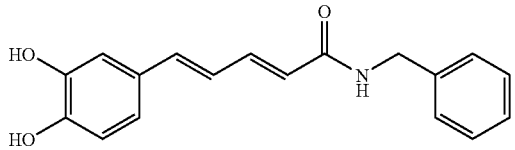

To a solution of 5-(4-hydroxy-3-methoxyphenyl)-penta-2,4-dienoic acid benzylamide (118 mg, 0.38 mmol) [Example 5] in 50 mL of dichloromethane, 100 µl of boron tribromide (0.95 mmol) was added dropwise at −78° C. The mixture was stirred for 15 min at −78° C. and for 1 h at room temperature. Water (100 ML) was added, the organic layer was separated, dried with $Na_2SO_4$ and evaporated.

The residue was purified by HPLC (column Nova-Pak C18 19.0×300 mm, MeCN—$H_2O$, 40:60, FR 10.0 mL/min, retention time is 9.6 min).

The results were as follows:
a. Yield 70 mg (63%).
b. UV, $\lambda_{max}$ 249 and 339 nm.
c. $^1$H-NMR (δ, ppm): 4.47 (s, 2H, $CH_2Ph'$), 6.17 (d, 1H, J=15.0 Hz, Hα olefinic), 6.80 (m, 3H, $H^5$+Hγ olefinic+ Hδ olefinic), 6.88 (dd, 1H, J 2.1 and 8.2 Hz, $H^6$), 7.05 (d, 1H, J=2.1 Hz, $H^2$), 7.22-7.36 (m, 6H, Ph'+Hβ olefinic).
d. MS (m/z, rel. intensity, %): 296.7 ([M+H]$^+$, 100), 318.4 ([M+$NH_4$]+, 50).

EXAMPLE 7

5-(4-Hydroxy-3,5-dimethoxyphenyl)-penta-2E,4E-dienoic acid 3,4-dihydroxybenzylamide (CRD-84)

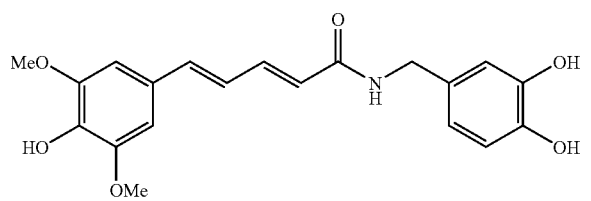

The compound was prepared based on the methodology in Example 5 using 38 mg (0.15 mmol) of 5-(4-hydroxy-3,5-dimethoxyphenyl)-penta-2E,4E-dienoic acid [Example 4], 67 mg (0.30 mmol) of 3,4 dihydroxybenzylamine hydrobromide, 153 µl (1.5 mmol) of triethylamine, and 100 mg (0.23 mmol) of BOP reagent.

The results were as follows:
a. Yield 31 mg (55%).
b. UV, $\lambda_{max}$ 253, 343 mm.
c. $^1$H-NMR (δ, ppm): 3.85 (s, 6H, $(OMe)_2$), 4.30 (s, 2H, $CH_2Ph'$), 6.16 (d, 1H, J=14.9 Hz, Hα olefinic), 6.62 (dd, 1H, J 2.1 and 8.0 Hz, $H^{6'}$), 6.73 (d, 1H, J=8.0 Hz, $H^{5'}$), 6.81 (d, 1H, J=2.1 Hz, $H^2$), 6.83 (d, 1H, J=15.5 Hz, Hβ olefinic), 6.88 (s, 2H, $^{H2+6}$), 6.90 (dd, 1H, J 10.4 and 15.5 Hz, Hγ olefinic), 7.33 (dd, 1H, J 10.4 and 14.9 Hz, Hβ olefinic).
d. MS (m/z, rel.intensity, %): 250.3 (15), 372.4 ([M+H]$^+$, 100), 394.0 ([M+$NH_4$]+, 38).

EXAMPLE 8

5-(4-Hydroxy-3-methoxyphenyl)-penta-2E,4E-dienoic acid 3,4-dihydroxybenzylamide (CRD-85)

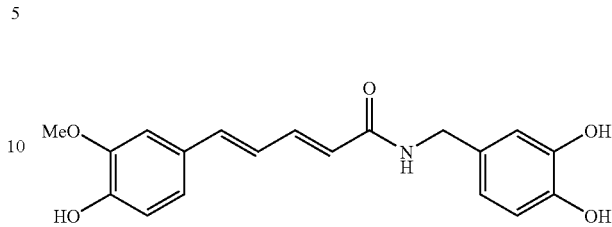

The compound was prepared as described in Example 5 using 11 mg (0.05 mmol) of 5-(4-hydroxy-3-methoxyphenyl)-penta-2E,4E-dienoic acid [Example 3], 22 mg (0.10 mmol) of 3,4 dihydroxybenzylamine hydrobromide, 50 g (0.50 mmol) of triethylamine, and 33 mg (0.075 mmol) of BOP reagent.

The results were as follows:
a. Yield 10.2 mg (60%)
b. UV, $\lambda_{max}$ 243, 339 mm.
c. MS (m/z, rel.intensity, %): 342.1 ([M+H]$^+$, 100), 359.0 ([M+$NH_4$]+, 28), 363.9 ([M+Na]$^+$, 40).

EXAMPLE 9

Killing of Philadelphia Positive Z119 Acute Lymphoblastic Leukemia Cells by Low-Dose Test Compounds in Culture Z119 cells were plated in 1 ml volumes at a density of 5×10$^4$ cells/ml, in the absence of exogenous growth factors, into 35 mm petri dishes (Nunc, Gibco) containing IMDM (OCI, Toronto) plus 20% FCS (Cansera Rexdale, ON.) in 0.9% (vol/vol) methylcellulose (Fluka, Switzerland) with the indicated concentration of for various test compounds described above. Cultures were set at 37° C., 5% $CO_2$ in a humidified atmosphere. Colonies consisting of more than 20 cells were counted at 7-9 days using an inverted microscope. The results for various test compounds described above are presented in Table 1.

EXAMPLE 10

Effect of Test Compounds Upon Normal Bone Marrow Differentiation in Culture

The CFU-GEMM assay was performed according to Fauser and Messner (1978, Blood, 52(6) 143-8) and Messner and Fausser (1980, Blut, 41(5) 327-33) with some variations. In brief, heparinized bone marrow cells were layered over Percoll (1.077 gm/ml) (Pharmacia Fine Chemical, Piscataway N.J.) and centrifuged at 400 g at 4° C. for 10 minutes to remove neutrophils and RBCs. The fractionated BM cells at 2×10$^{-5}$ cells/ml were cultured in IMDM (OCI, Toronto) containing 0.9% (vol/vol) methylcellulose supplemented with 30% FCS (Cansera Rexdale, ON.) or normal human plasma, a cocktail of cytokines containing G-CSF (10 ng/ml, Amgen), IL-3 (40 U/ml, Immunex), MGF (50 ng/ml, Immunex), Erythropoietin (2 u/ml, Epprex) or TPO (10 ng/ml, Amgen), 5×10$^{-5}$ M Bβ-2-mercaptoethanol and the specified concentration of CR4. The culture mixture was plated in 1 ml volumes into 35 mm petri dishes and incubated at 37° C., 5% $CO_2$ in a humidified atmosphere. All cultures were evaluated at 14 days for the number of BFU-E colonies (defined as aggregates of more than 500 hemoglobinized cells or, 3 or more erythroid subcolonies), CFU-GM colonies (defined as granulocyte or monocyte-macrophage cells or both), CFU-Meg colonies (comprising 4 or more megakaryocytes) and CFU-GEMM colonies (a mixed population comprising of all elements). The results for various test compounds described above are presented in Table 1.

While the results in Table 1 for many of the test compounds are good, it is believed that the best results are those reported for compound CRD-82.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. For example, many of the specific compounds of the present invention are encompassed by the general compounds of the Formula I. For the purposes of 35 U.S.C. §112 (first paragraph) and Article 123(2)/(3) EPC, it should be understood that the use of general compounds of the Formula I is shorthand for listing each specific compound encompassed thereby. Thus, general compounds of the Formula I are to be considered substantively identical to a list of specific compounds derived from all permutations and combinations covered by a general compound. As such, for the purposes of 35 U.S.C. §112 (first paragraph) and Article 123(2)/(3) EPC, the right to use one or more provisos or disclaimers to clarify the definition of a general formula is expressly reserved (i.e., having the effect of selecting members of a list of specific compounds derived from a general compound). It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

TABLE 1

| Code | ALL (Z 119) IC50, µM | NBM (BFU-E) IC50, µM |
|---|---|---|
| CRD-81 | >1.0 | >>10 |
| CRD-82 | =0.46 | >25 |
| CRD-84 | >1.0 | >>10 |
| CRD-85 | >1.0 | >>10 |

What is claimed is:

1. A method of treating acute lymphoblastic leukaemia in an animal in need of treatment thereof comprising the step of administering an effective amount of a compound of Formula I, and salts, solvates and hydrates thereof:

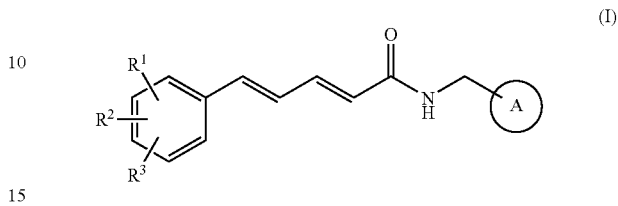

wherein:

$R^1$, $R^2$ and $R^3$ are each independently selected from OH, $C_{1-6}$alkyl, $OC_{1-6}$alkyl, $OC(O)C_{1-6}$alkyl, $C(O)OC_{1-6}$alkyl, $NH_2$, NH—$C_{1-6}$alkyl, $N(C_{1-6}$alkyl$)(C_{1-6}$alkyl$)$, $C(O)NHC_{1-6}$alkyl, $C(O)N(C_{1-6}$alkyl$)(C_{1-6}$alkyl$)$, SH, $SC_{1-6}$alkyl, $NO_2$, $CF_3$, $OCF_3$ and halogen; and A is an aromatic or heteroaromatic group chosen from benzene, naphthalene, quinoline, isoquinoline, indole, pyridine, pyrasine, pyrimidine, imidazole, furan and thiophene, unsubstituted or substituted with 1-4 substituents independently selected from OH, $C_{1-6}$alkyl, $C_{1-6}$alkoxy, $C_{1-3}$alkylenedioxy, $NH_2$, NH—$C_{1-6}$alkyl, $N(C_{1-6}$alkyl$)(C_{1-6}$alkyl$)$, SH, S—$C_{1-6}$alkyl, $NO_2$, $CF_3$, $OCF_3$ and halogen.

2. The method defined in claim 1, wherein the compound of Formula 1 is 5-(4-hydroxy-3-methoxyphenyl)-penta-2E,4E-dienoic acid benzylamide (CRD-81), a salt thereof, a solvate thereof or a hydrate thereof.

3. The method defined in claim 1, wherein the compound of Formula I is 5-(3,4-dihydroxyphenyl)-penta-2E,4E-dienoic acid benzylamide (CRD82), a salt thereof, a solvate thereof or a hydrate thereof.

4. The method defined in claim 1, wherein the compound of Formula I is 5-(4-hydroxy-3,5-dimethoxyphenyl)-penta-2E,4E-dienoic acid 3,4-dihydroxybenzylamide (CRD-84), a salt thereof, a solvate thereof or a hydrate thereof.

5. The method defined in claim 1, wherein the compound of Formula I is 5-(4-Hydroxy-3-methoxyphenyl)-penta-2E,4E-dienoic acid 3,4-dihydroxyberizylamide (CRD-85), a salt thereof, a solvate thereof or a hydrate thereof.

* * * * *